United States Patent [19]
Cattorini et al.

[11] Patent Number: 5,864,601
[45] Date of Patent: Jan. 26, 1999

[54] METHOD AND APPARATUS FOR INSPECTING PIPES USING A DIGITIZED RADIOGRAPH

[75] Inventors: Joseph Francis Cattorini; Richard Walter Franzen, both of Melbourne; David Walter Hicks, Melbourne Beach; David Herbert Riley, Rockledge, all of Fla.

[73] Assignee: DBA Systems, Inc., Melbourne, Fla.

[21] Appl. No.: 662,307

[22] Filed: Jun. 13, 1996

[51] Int. Cl.⁶ .......................... G01N 17/00; G01N 23/18
[52] U.S. Cl. ................................ 378/59; 378/54; 378/62
[58] Field of Search .................................. 73/86; 378/54, 378/58, 59, 62, 901

[56] References Cited

U.S. PATENT DOCUMENTS

| | | | |
|---|---|---|---|
| 4,323,973 | 4/1982 | Greenfield | 364/515 |
| 4,368,996 | 1/1983 | Davis et al. | 403/5 |
| 4,649,559 | 3/1987 | Wang | 378/146 |
| 4,692,936 | 9/1987 | Billeaudeaux | 378/59 |
| 4,779,453 | 10/1988 | Hopenfeld | 73/86 |
| 4,922,748 | 5/1990 | Hopenfeld | 73/86 |
| 4,922,915 | 5/1990 | Arnold et al. | 378/18 X |
| 4,935,195 | 6/1990 | Palusamy et al. | 376/249 |
| 4,974,246 | 11/1990 | Heiskel | 378/59 |
| 5,179,579 | 1/1993 | Dove | 378/38 |
| 5,187,542 | 2/1993 | Madzsar | 73/86 X |
| 5,210,783 | 5/1993 | Wallace | 378/207 |
| 5,377,533 | 1/1995 | Shaw et al. | 73/86 |
| 5,410,144 | 4/1995 | Lavelle et al. | 250/208.1 |
| 5,447,057 | 9/1995 | Shaw et al. | 73/86 |

*Primary Examiner*—Thomas P. Noland
*Attorney, Agent, or Firm*—Pollock, Vande Sande & Priddy

[57] ABSTRACT

An apparatus and method using non-destructive testing and evaluation analyzes pipes to accurately measure the depth of corrosion and/or erosion in the pipe. Two penetrameter shims are attached to the outside surface of the pipe near the area of corrosion. Then, a radiograph of the pipe in the area of corrosion is generated using an X-ray source and an X-ray sensitive film. The radiograph is subsequently digitized, and the digital information is entered into a computer. A computer operator (user) is then asked to input several parameters concerning the diameter of the pipe, the thickness of the shims, etc., using, for example, a keyboard and to select the areas of interest using, for example, a computer mouse. All the while the computer operator is navigated through several user-friendly screens in a window environment driven by a Graphical User Interface. After all the required user input is entered into the computer program, the extent of corrosion in the area indicated by a cursor is displayed on the screen. In addition, the remaining wall thickness of the pipe is also indicated to the operator.

13 Claims, 6 Drawing Sheets

| PIPE | SHIM 10 | SHIM 20 |
|------|---------|---------|
| .5"  | .010"   | .09"    |
| 1.5" | .010"   | .09"    |
| 3.0" | .010"   | .12"    |
| 8.0" | .020"   | .09"    |

FIG. 8

METHOD AND APPARATUS FOR INSPECTING PIPES USING A DIGITIZED RADIOGRAPH

FIELD OF THE INVENTION

This invention relates to non-destructive testing and evaluation of pipes and, in particular, a method and apparatus for analyzing the condition of a pipe, i.e., measuring the depth of corrosion and/or erosion. The inventive method and apparatus employ software modules including a Graphical User Interface to enable a user to quickly and precisely analyze a radiograph of the pipe generated by an X-ray source and subsequently digitized for processing by a computer.

BACKGROUND OF THE INVENTION

Non-destructive testing and evaluation are well known and commonly used in various economic sectors of the world. Some examples of non-destructive testing and evaluation using gamma rays or ultrasound, for example, span the full range of industrial, biomedical, and research applications. Industrial applications involving hazardous materials are especially suitable for such testing and evaluation.

Inspection of pipes, carrying hazardous fluids or located in a hazardous environment, for signs of corrosion and/or erosion is one industrial application which is widely embraced by many companies. For example, pipes on nuclear submarines are regularly subjected to inspection for an early detection of corrosion and erosion. Radiographs of virtually every pipe in a nuclear submarine are obtained on a regular basis and examined by trained personnel. When a radiograph of a pipe shows some dark spots or shadows, signifying possible scattering or absorption of the incident X-rays as opposed to those transmitted through the pipe, it is a sign of possible corrosion or erosion in the pipe.

Obviously, replacing a pipe is not economically feasible even if possible corrosion or erosion is detected, because the extent of damage to the pipe may be negligible without posing any significant danger. The damaged pipe may be quite safe still fully conforming to the standards determined to be acceptable under particular conditions. In many situations, the damaged pipe may safely operate for a long period of time after the detection of the corrosion or erosion if the wall is still sufficiently thick. It is therefore apparent that the depth of the corrosion or, alternatively, the remaining wall thickness of the pipe is critically important and must be determined with high precision when the radiograph of the pipe reveals some signs of corrosion in certain spots.

Currently, after taking a radiograph, the area of the pipe showing corrosion is further inspected using ultrasound echo probes, for example, to more precisely determine the remaining wall thickness. This entails carrying an ultrasound equipment onto the submarine and preparing the area of the pipe for an ultrasound image. If the image shows that the corroded pipe does not require any repair or replacement, this procedure must be repeated at the next scheduled inspection. The pipe is thus closely monitored during the scheduled periodic inspections until it is determined that the corrosion or erosion poses a sufficient threat to the proper operation of the pipe.

It is apparent that the above procedure to determine the exact depth of corrosion or erosion has several significant drawbacks. First, the additional step of an ultrasound imaging is cumbersome and poses inconvenience to the inspecting personnel, including preparing the site again for inspection and carrying additional equipment thereto. Second, if facility is radioactive as is the case with a nuclear submarine, the inspecting personnel is subjected to the additional radiation exposure. Third, the ultrasonic measurements are not sufficiently accurate to provide the precise extent of the pipe corrosion.

Therefore, a need in the field of non-destructive testing and evaluation exists for a method and apparatus for pipe inspection that overcomes the above disadvantages.

SUMMARY OF THE INVENTION

It is therefore an object of the present invention to determine the wall thickness of pipes, i.e., the extent of corrosion or erosion, using digitized radiographs in a user-friendly environment.

It is another object of the present invention to determine with high precision the wall thickness of pipes experiencing some corrosion or erosion.

These and other objects, features and advantages are accomplished by a non-destructive testing apparatus which measures corrosion or erosion in an object. The apparatus includes a radiation source adjacent the object for emitting rays directed at the object. A radiation sensitive film is located substantially across and beyond the object from the radiation source for receiving the rays to produce a radiograph of the object. A pair of shims is attached to the object in a corrosion area between the film and the object for determining a mass attenuation coefficient of the object and a conversion factor between density and thickness of the object. A scanner/digitizer generates digital information representing the object and the pair of shims based on the radiograph. A graphical image of the object and the pair of shims is then displayed based on then digital information. The graphical image is subsequently processed by a computer to obtain a numerical value representing the extent of corrosion in the object or, alternatively, a second numerical value representing the remaining wall thickness of the object.

BRIEF DESCRIPTION OF THE DRAWINGS

The above-mentioned as well as additional advantages and features of the present invention will be evident and more clearly understood when considered in conjunction with the accompanying drawings, in which.

In all Figures, like reference numerals represent same or identical components of the present invention.

DESCRIPTION OF THE PREFERRED EMBODIMENTS

As a general overview, the present invention uses non-destructive testing and evaluation to analyze pipes and, in particular, to accurately measure the depth of corrosion and/or erosion in the pipe. Two shims are employed to detect the wall thickness of the pipe on a relative basis.

In accordance with the inventive method and apparatus, once the corrosion of the pipe is detected, two penetrameter shims, alternatively known as Image Quality Indicator (IQI) test pieces, are attached to the outside surface of the pipe near the area of corrosion. The shims may be representatively attached with a tape or non-metal strap wrapped around the pipe at the location of the corrosion as indicated on the radiograph. Then, a radiograph of the pipe in the area of corrosion is generated using an X-ray source and an X-ray sensitive film. The radiograph is subsequently digitized using gray scale scanning and conversion technique.

After the information comprising the digitized radiograph is entered into a computer, an image of the pipe, corrosion area and shims appears on the computer screen using an image-generating, windows-driven computer program. A computer operator (user) is then asked to input several parameters concerning the diameter of the pipe, the thickness of the shims, etc., using, for example, a keyboard and to select areas of interest on the pipe image using, for example, a computer mouse. All the while the computer operator is navigated through several user-friendly screens in a window environment driven by a Graphical User Interface. After all the required user input is entered into the computer program, the extent of corrosion, measured in metric or U.S. units, in the area indicated by a cursor is displayed on the screen. In addition, the remaining wall thickness of the pipe is also indicated to the operator.

Additional measurements of corrosion and wall thickness within the same general area depicted on the radiograph can be easily repeated by selecting new sites via a mouse click. Since the setup parameters requiring the user input are already contained in the computer memory, new measurements can be quickly and easily performed with a simple mouse click to select and analyze the new site in the area of corrosion.

Figure 1:
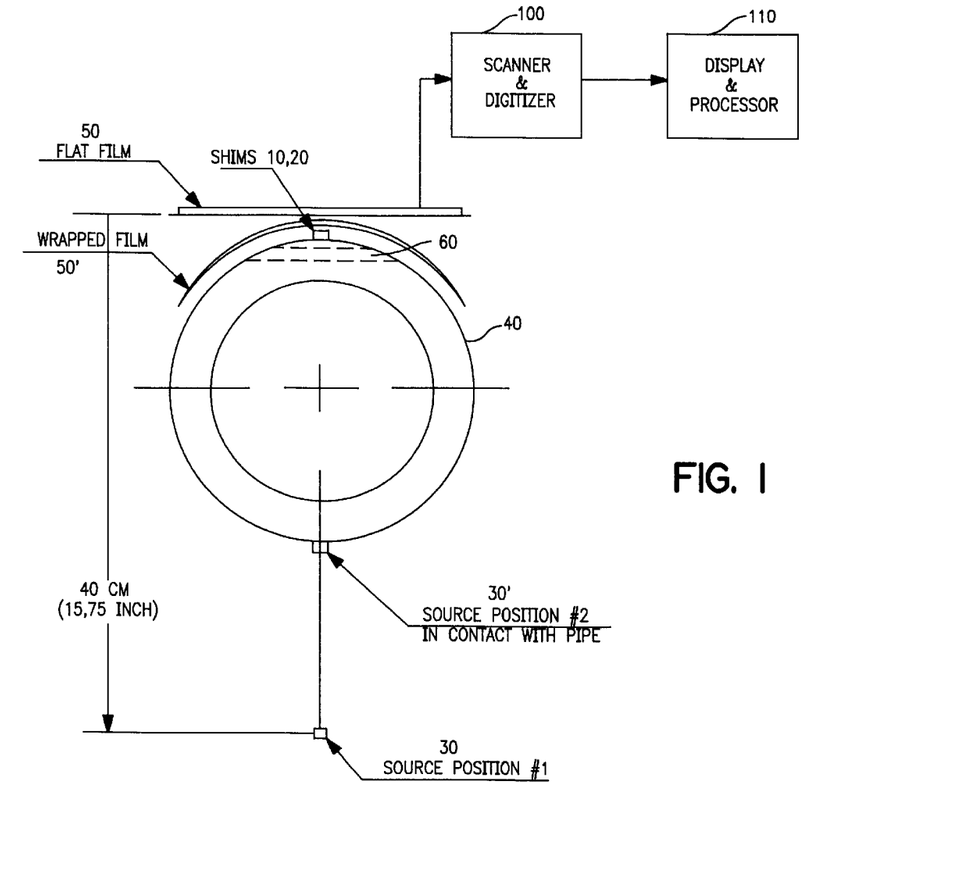
FIG. 1 shows a block diagram of the configuration setup comprising a pipe, shims, an X-ray source, a film, a scanner/digitizer and a display/processor for inspecting corrosion in the pipe in accordance with one embodiment of the present invention.

Next, the preferred embodiment of the present invention will be described in detail with reference to FIGS. 1–7. FIG. 1 shows an axial view of a pipe 40 having some corrosion in it, as indicated by the area 60 bounded by two dashed lines. To determine the remaining wall thickness of the pipe 40, two penetrameter shims 10, 20 are attached to the pipe 40 in the general area of corrosion. Depending on such factors as the pipe size, the physical location of the pipe and the area of corrosion with respect to other adjoining elements, the available space surrounding the pipe, as well as other physical factors and logistical considerations, a film 50 may be placed flat against or beyond the pipe 40. Alternatively, a film 50' may be wrapped around the pipe 40 as shown in FIG. 1. Substantially the same considerations and physical factors used in deciding whether to use flat or wrapped film may influence the decision on whether an X-ray source 30 is placed at some distance from the pipe 40 or in contact with it as represented by a source 30' in FIG. 1. Although FIG. 1 indicates that the distance between the films 50, 50' and the X-ray source 30 is approximately 40 cm (15.75 inches), it is clearly understood that the selected distance is exemplary only. Other distances may be used without departing from the spirit of the present invention.

Also shown in FIG. 1 are a scanner/digitizer 100 for scanning and digitizing the radiograph to produce digital information representing the pipe and shims. An image display and processor 110 are connected to the scanner/digitizer 100 for generating an image of the object and shims based on the digital information, and for processing the image to obtain a numerical value representing the extent of corrosion the pipe 40. This will be fully explained below.

Figure 2:
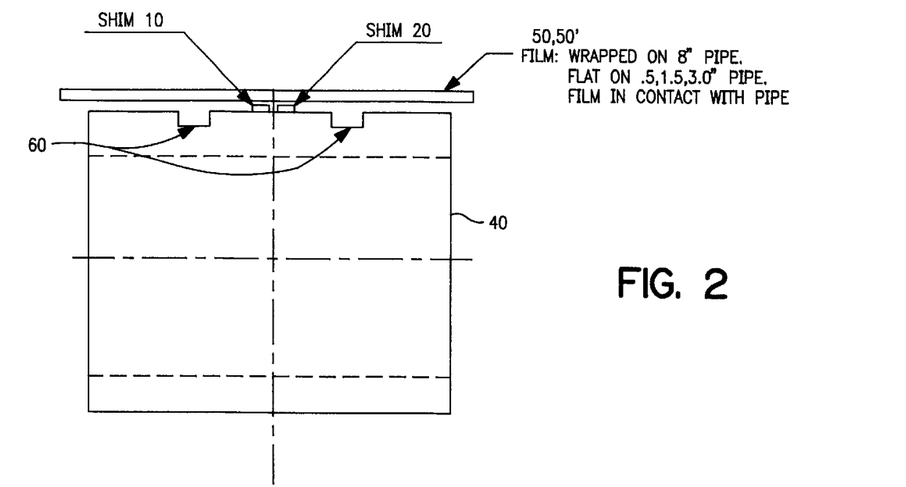
FIG. 2 shows an enlarged view of a portion of the diagram, i.e., a Region of Interest, depicted in FIG. 1.

FIG. 2 shows a transaxial view of the pipe 40 and, in particular, an enlarged view of the area of interest containing shims 10, 20 in the area of simulated corrosion 60. Two shims are now clearly visible in FIG. 2: the shim 10 is thinner than the shim 20, and are both placed close to the centerline of the pipe 40. In one representative embodiment, the film 50' is wrapped around an 8-inch pipe, while in other embodiments the film 50 is positioned flat against 0.5, 1.5 and 3-inch pipes. Although in all these embodiments, the films 50, 50' are in contact with the pipe undergoing the inspection, it is understood that films located at some distance from the pipe, i.e., not in contact with the pipe, may also be used in accordance with the present invention.

Next, a radiograph of the corrosion area containing the shims 10, 20 is produced as known in the art. X-ray energy emitted by the source 30 or 30' may be scattered, absorbed by the pipe and shims, or transmitted through those elements onto the film. The emission of the X-radiation from the source is recorded on the radiation sensitive films 50, 50' to produce an image indicating, in particular, the area of interest, i.e., the corrosion area. Either negative or positive film may be used to generate images, as well known in the art.

The radiograph is then scanned and digitized using, for example, a 16-bit radiometric resolution scanner. The digital information comprising the radiograph is subsequently input into a computer. An image of the pipe, based on the scanned and digitized radiograph, is shown in FIG. 3.

Figure 3:
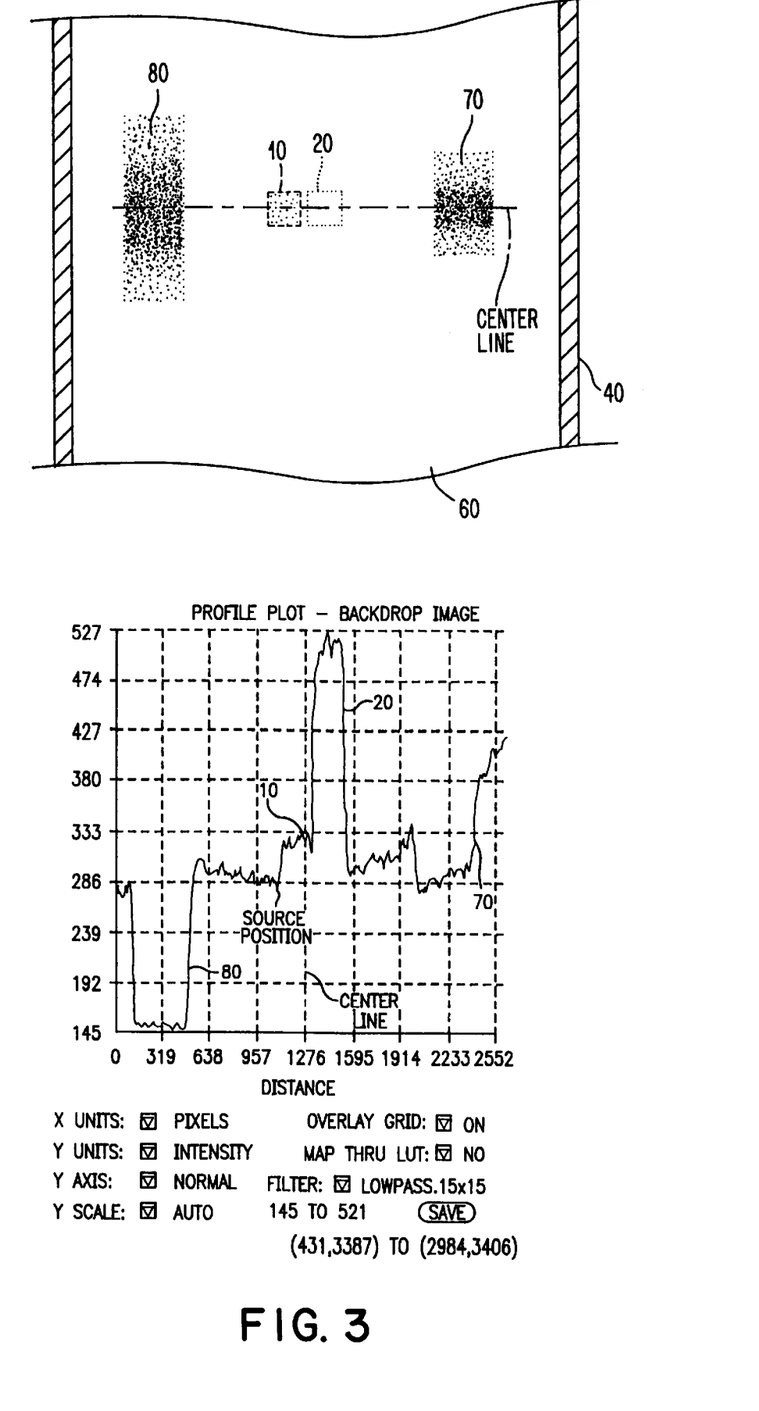
FIGS. 3–6 show computer screen images of the windows-driven program as the user analyzes the areas of corrosion based on the digitized radiograph of the pipe.

To achieve the image in FIG. 3, a ZOOM operation of the Backdrop Image to Screen is performed with the 1:1 ratio using the Graphical User Interface Module. The 1:1 ratio means that a single screen pixel corresponds to only one pixel of the digitized radiograph. The ZOOMed view is then converted to a Region of Interest for subsequent annotation by the user as explained below. Thus, FIG. 3 represents a screen image entitled "BACKDROP IMAGE: ACTIVE" showing a portion of the pipe 40 containing the general area of corrosion 60. The two shims 10, 20 are also displayed: the thick shim 20 appears brighter than the thin shim 10, which is a little brighter than the background. To provide an easier identification of the thin shim 10, dashed lines were added to FIG. 3 around the perimeter of the shim 10. Dark spots 70 and 80 designate areas of corrosion where the remaining wall thickness of the pipe is of utmost concern to the inspecting personnel.

Using any of the known computer input devices, such as the mouse for example, the operator then draws a line passing through the central axis of the pipe. If this line does not pass through the shims, a second line is drawn. This line must be parallel to the central axis of the pipe and pass through the shims. The second line may be necessary because the shims could not be accurately taped or attached to the center of the pipe during the setup, or alternatively the source was accidentally positioned at an angle to the pipe.

Next, a Profile Plot of the Backdrop Image is displayed on the screen, as shown in FIG. 3. Various options may be specified by the user to generate the Profile Plot. For example, to reduce the imaging effects of the pipe texture, the image is passed through a 15 by 15 pixel low pass filter to smooth out the graph. The auto-Y scale option automatically justifies the image between the highest and the lowest intensity values to allow the user to concentrate on the Region of Interest. Typically, the overlay grid is turned on.

In FIG. 3, the y-axis is the intensity represented by digital values, and the x-axis is the distance also represented by digital values.

The Profile Plot focuses on the general area of corrosion 60, proceeding from left to right of the Backdrop Image along the central axis of the pipe 40. The Profile Plot displays the two deep corrosion spots 70, 80 having low intensity values (dark spots on the Backdrop Image). The two shims 10, 20, which appear as bright spots on the Backdrop Image, have high intensity values on the Profile Plot.

Among other things, the Profile Plot is used to determine the actual position of the X-ray source. Although it is required to position the X-ray source along the centerline of the pipe, the actual position may be off center due to setup inaccuracies. To account for such imperfect source positioning, the user looks for the darkest, i.e., lowest, position on the pipe Profile Plot while disregarding the two corrosion spots. For example, the source position based on the Profile Plot in FIG. 3 appears to be slightly to the side of the thick shim 10, and not exactly in the center of the pipe. The exact source position is important since the program calculates the wall thickness based on the distance from the radiation source, the physical shape of the object (i.e., a pipe, plate, etc.), as well as geometrical configuration of the source with respect to the object. This will be more fully explained below in connection with the software modules of the present invention. The same procedure of establishing the source position is repeated in the other direction of the pipe, i.e., the Profile Plot is generated with the vertical centerline instead of horizontal.

Figure 4:
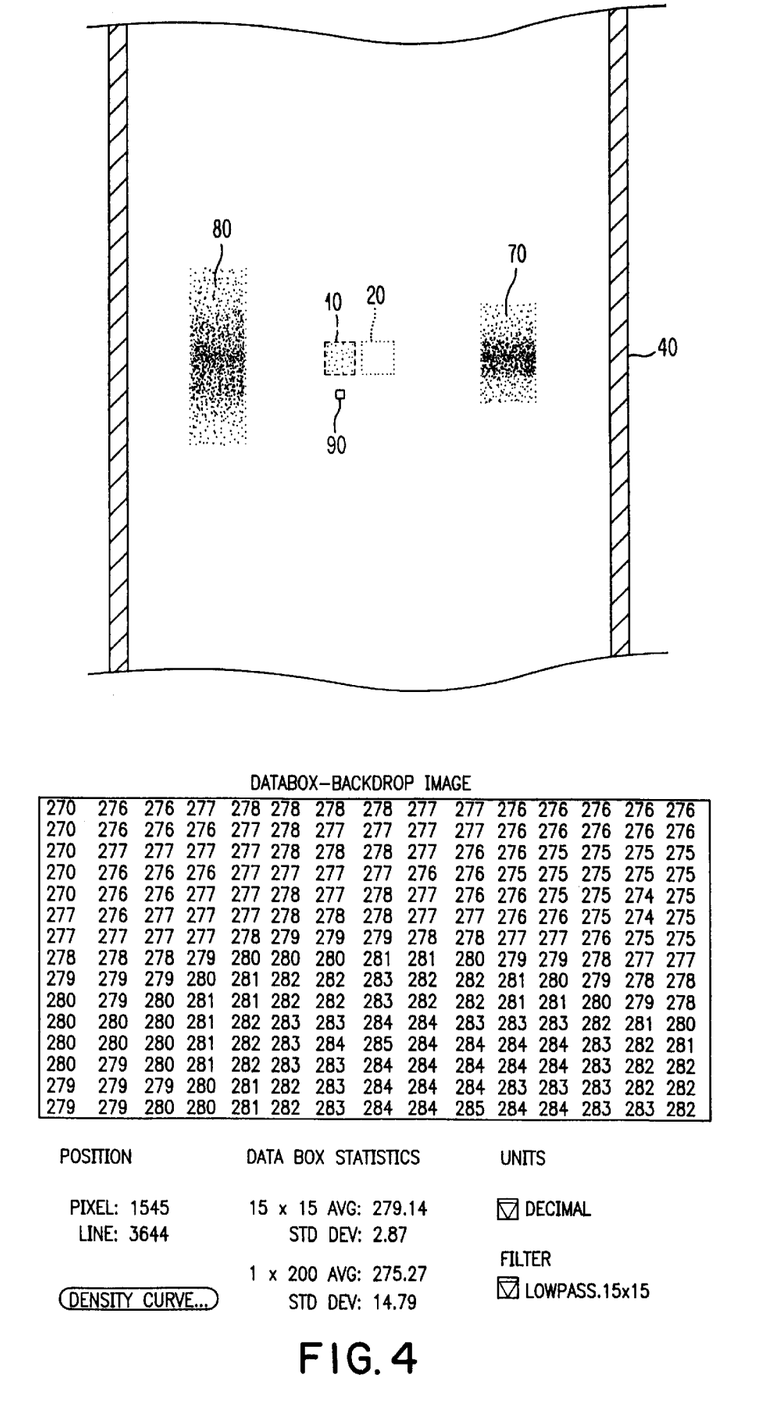

Next, the user selects the Databox screen from the menu selection to place the previously determined source position on the screen image, as shown in FIG. 4. Based on the previous step of determining the source position using the Profile Plots and Backdrop Images, the operator uses a computer input device to put a graphical representation of the databox 90, which is a 15 by 15 pixel frame, at the bottom and slightly to the left of the thick shim 20, as shown in FIG. 4. Once placed on the screen at the proper location, the pixel and line position of the databox 90 appears on the screen. In this exemplary embodiment of the present invention, the source position is located at pixel 1545 and line 3644. This position is recorded by the user for future entry as explained next.

Figure 5:
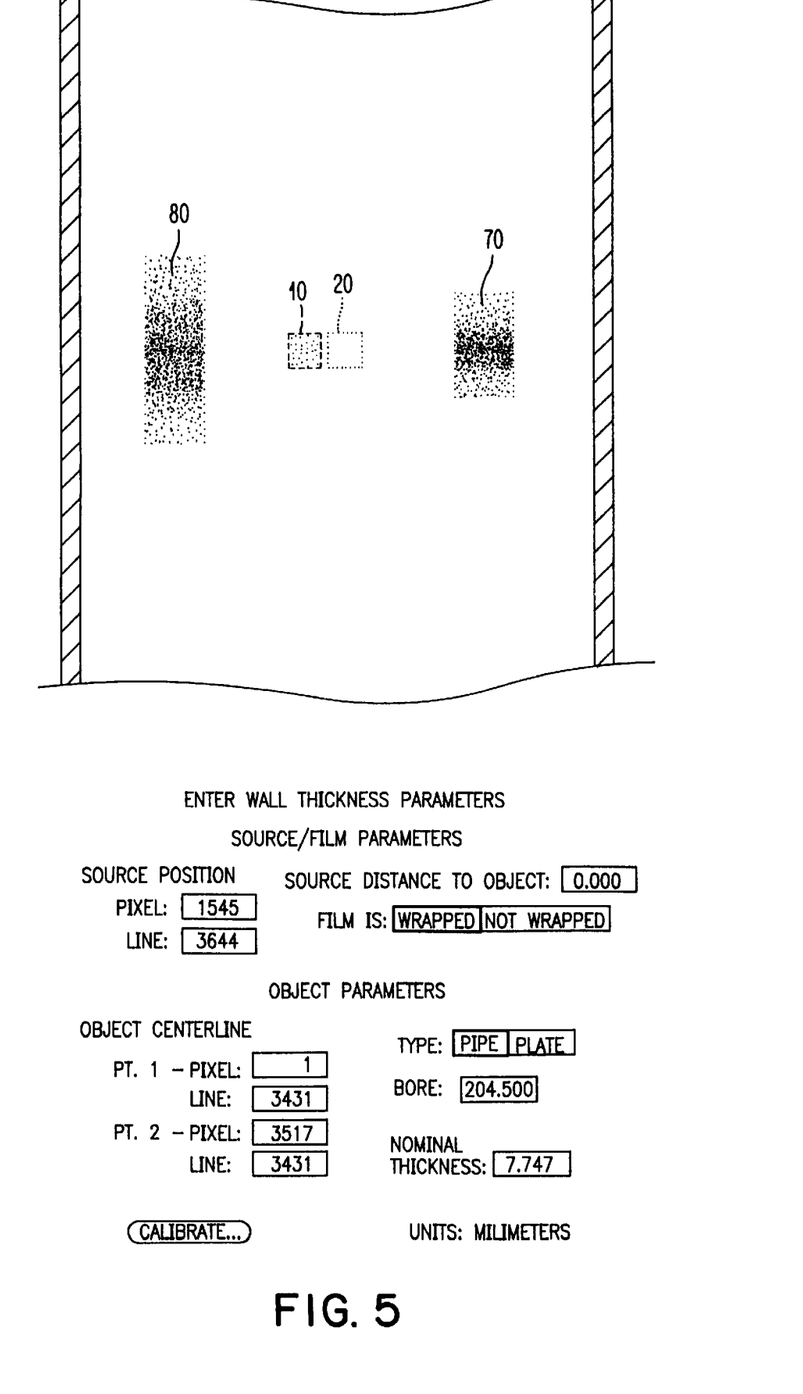

The user then selects the Wall Thickness Parameters screen from the menu, as shown in FIG. 5. The user is prompted for the source position (previously recorded as 1545 and 3644) which is now inserted in a numerical form on the appropriate lines. As stated above, the source position defines the location of the source relative to the radiograph. In addition, other source/film parameters, such as the source distance to object, whether the film is wrapped or not, the type of the object, are entered by the user in response to the prompts from the program. If the film is not wrapped, the user is requested to enter a distance from the film to the object. If, however, the film is wrapped, i.e., in contact with the object, then the distance is zero. In addition, if the object type is pipe, then the bore size must be entered, while this parameter is inapplicable if the object type is a plate.

These parameters are based on the predetermined setup configuration, and either known to the user or determined in the previous steps as explained above. One other parameter requested from the user is an object centerline which must be determined based on the Profile Plot. The object centerline is the axial centerline of the pipe. Two points are selected from the Profile Plot to define the angle at which the radiograph is taken with respect to the pipe centerline. In this exemplary embodiment, the object (pipe) centerline is substantially horizontal.

It is worth noting that FIG. 5 displays all measurements in millimeters. Although the program defaults to millimeters, the option of changing the reference units to inches is available.

Figure 6:
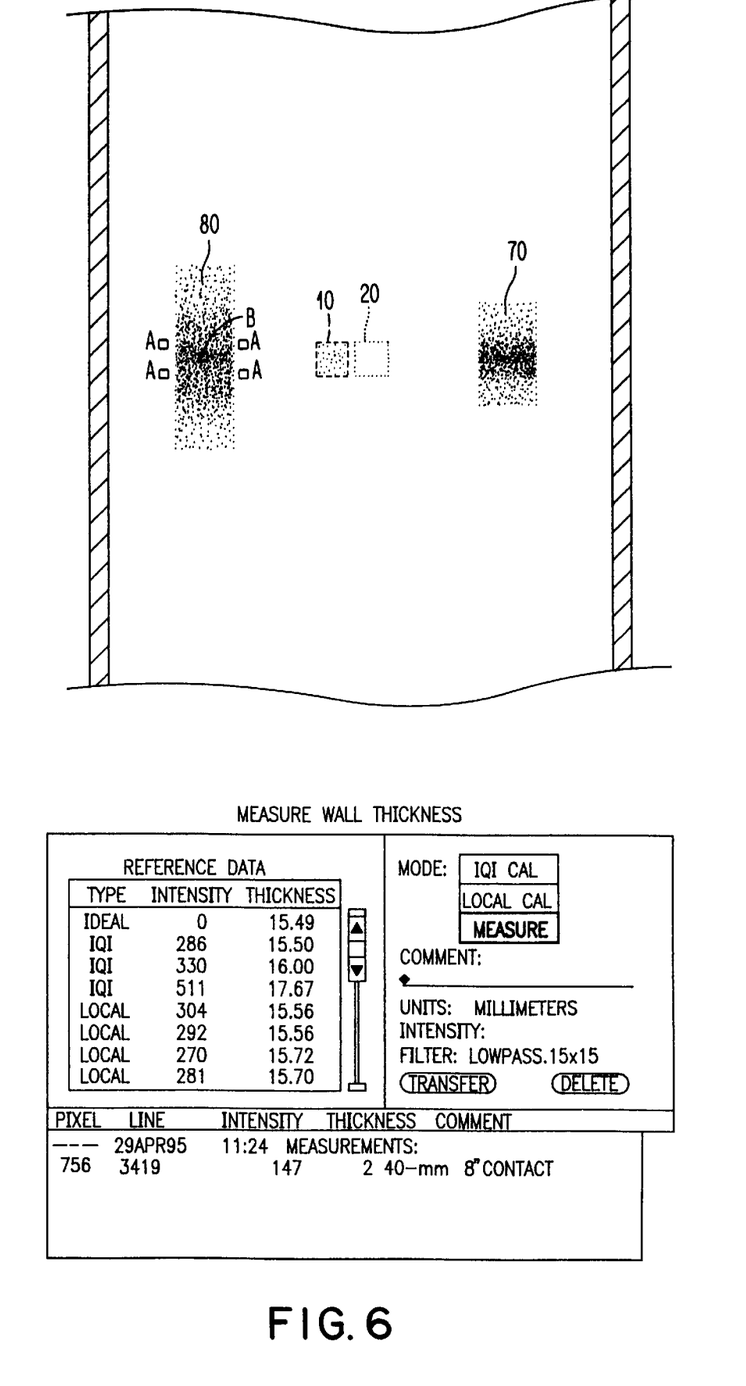

After all parameters are filled in, the calibration procedure is started by activating the "Calibrate" button on the screen. The computer screen is shown in FIG. 6 after the activation of the "Calibrate" button. At this point, the "IQI Cal" button on the screen image is selected to calibrate the quality indicators (penetrameter shims that were installed on the pipe). The "IQI Cal" generates a 15 by 15 pixel frame that appears on the active image. The average value of these 225 pixels is used for calibration by the program. The pixel frame is then substantially centered over one of the penetrameter shims, and the shim thickness is entered by the user. After that, the "Transfer" button on the screen image is selected. The other shim is addressed in a similar manner. Finally, a third IQI test piece is selected representing an uncorroded pipe area, and its thickness of 0.0 is entered as a parameter.

Next, the "Local Cal" mode is activated. Again, the pixel frame appears on the active image to calibrate undamaged areas near the eroded area of interest. At least two points surrounding the eroded area should be selected. In this exemplary embodiment, four points are selected as indicated by reference characters "A" in FIG. 6. The points must be selected just outside the area of interest, i.e., uncorroded area of the pipe. After that step, the "Transfer" button is activated.

Finally, the "Measure" mode is chosen. Again, the pixel frame appears on the screen and may be placed anywhere in the corrosion area as represented by the image. In this exemplary embodiment, the point designated by a reference character "B" is chosen within the area 80. The remaining total thickness (the distance between the uncorroded top wall and the corroded bottom wall) is displayed on the screen. Additionally, the depth of corrosion is shown to the user.

Under one experimental setup using pipes, the measurement point designated as "B" was in the middle of the simulated erosion area 80. The actual erosion was 2.21 mm, while the result obtained in accordance with the present invention was 2.40 mm.

To determine the plate and/or pipe wall thickness and the accompanying extent of corrosion, another experimental set-up comprising a set of plates, instead of pipes, with machined incremental counterbores was designed to simulate the pipe walls and the corrosion therein. Three calibration plate sets were prepared, representing 0.75-inch, 3-inch and 8-inch pipe sizes. Radiographs of these plates were subsequently generated. The radiographs were further digitized with a 16-bit scanner. The digitized data was used to predict the depth of the plate counterbores. Accuracy of 0.1 mm was generally achieved.

If the user wishes to analyze another erosion area on the same radiograph, the local calibration points, i.e., "A" points, are deleted using the "Delete" button on the screen image. New local calibration points are then selected, and the area of erosion is measured thereafter. Since all the information regarding the physical configuration of the setup has been previously entered by the user during the initial measurement, the new measurements can be repeated quickly and easily by simply clicking on the points of interest.

Figure 7:
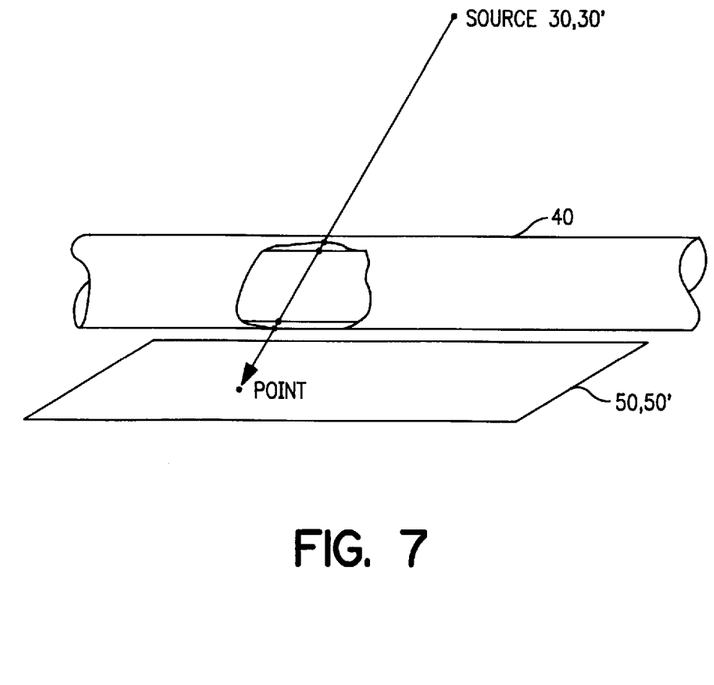
FIG. 7 shows a representative configuration setup comprising the pipe, the X-ray source and the film to illustrate computations for "apparent" pipe thickness.

The software modules will now be described in accordance with the present invention. Module A is a geometry software that calculates "apparent" pipe (object) thickness, i.e., the distance that the ray travels through the pipe from the radiation source to the film. Such factors as the source location, film location and pipe (object) dimensions are taken into account when calculating the "apparent" object thickness. This computation proceeds as follows with reference to a representative setup shown in FIG. 7. First, a three-dimensional position of the source 30 or 30' is computed. Next, a three-dimensional position of a point on the film 50 or 50' is calculated. Finally, "apparent" pipe thickness is calculated by intersecting source/point three-dimensional vectors with pipe cylinders. The intersection of source/point vector with inner and outer cylinders, as shown in FIG. 7, yields four intersections. The "apparent" pipe thickness is then equal the outside diameter minus the inside diameter.

Module B contains the equation for mass attenuation coefficient. The thin (small) shim is used to establish the mass attenuation coefficient, which indicates how much the pipe is absorbing radiation. The basic equation relating radioactive intensity to the object thickness is given by:

$$I = I_0 e^{-\mu_m p t}, \tag{1}$$

where $I$ == intensity measured at a detector (film) after the object penetration $I_0$ == intensity measured at a detector (film) without the object $\mu_m$ == mass attenuation coefficient p == object density t == object thickness Differentiating the above equation yields:

$$\Delta I/I = \mu_m p \Delta t_{gs} \tag{2}$$

Since the intensity is directly proportional to gray scale (gs):

$$\Delta \Delta gs/gs = \mu_m p \Delta t_{gs}, \tag{3}$$

where gs == gray scale value $\Delta t_{gs}$ == object thickness based upon gs

The above equation (3) is contained in the Module B, which calculates the mass attenuation coefficient using "apparent" gray scale thickness of the thin shim obtained from Module A.

Module C converts the "apparent" gray scale thickness of Module B into a "physical" thickness using the thick shim, since gray scale difference does not represent a physical difference. The thick (large) shim provides a correlation between density and the wall thickness of the pipe. This conversion factor is needed since density does not vary linearly as wall thickness does. Thus, the thick shim establishes an exponential relationship between density and wall thickness of the pipe. The conversion factor is the variable m in the equation (4):

$$t_{phys} = t_{gs} e^{m t_{gs}} \tag{4}$$

Module D is the Graphical User Interface which converts the radiograph image into physical dimensions while taking into account image resolution, zoom factor, angular orientation, etc. In addition, this Module provides the windows and user interface screens as explained above in connection with FIGS. 3–6.

The operational sequence of steps in accordance with the method of the present invention is as follows. First, the user inputs the test setup parameters to generate and define the radiograph. These parameters flow into modules A and D. Next, the user inputs data into Module B to determine the mass attenuation coefficient by placing, for example, a cursor or pixel frame over the appropriate shim and pipe (object) areas. Then, the user inputs data into Module C to determine the conversion factor between the gray scale and physical thickness by placing a cursor or pixel frame over the appropriate shim and pipe (object) areas. Finally, the user inputs data to measure wall thickness (and hence corrosion) by placing a cursor or pixel frame over selected areas of the pipe (object). Modules B and C calculate "physical" thickness based on the mass attenuation coefficient and the gray scale conversion factor determined in previous steps.

It is important to note that the complete program is menu-driven which navigates the user through the necessary steps to obtain the desired results.

Figure 8:
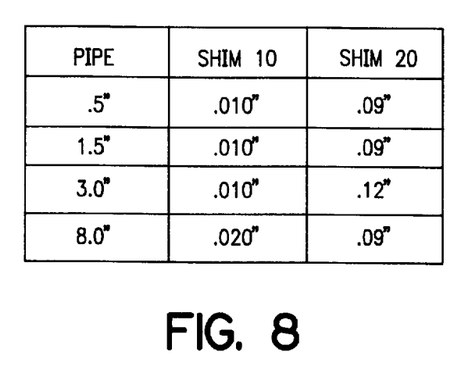
FIG. 8 shows a table with various pipe sizes and representative thicknesses of the shims used on those pipes to enable the measurement of the extent of corrosion.

Another important consideration is that both shims must be made of the same material as the object under inspection. In one representative embodiment of the present invention, the size of the shims was approximately 0.25 by 0.25 inches, i.e., pieces of metal made of the same material as the pipe. While the thickness of the thin shim should be selected as thin as possible to distinguish it from the roughness of the pipe which is about 0.001 inches, in one embodiment the thickness of the thin shim was about 0.008 of an inch. In other embodiments, thin shims having the thickness of about 0.01–0.02 inches produced acceptable results. FIG. 8 shows some representative shims, i.e., thin shims designated as 10 and thick shims designated as 20, used on various pipe sizes.

The present invention applies to various sizes and materials of pipes and plates, radiation sources, source-to-film distances, positions of the film with respect to the pipe/plate, and film types.

Since those skilled in the art can modify the disclosed specific embodiment without departing from the spirit of the invention, it is, therefore, intended that the claims be interpreted to cover such modifications and equivalents.

What is claimed is:

1. A non-destructive testing apparatus for measuring corrosion or erosion in an object, comprising:

a radiation source adjacent said object for emitting rays directed at said object;

a radiation sensitive film located substantially across and beyond said object from said radiation source for receiving said rays to produce a radiograph of said object;

a pair of shims attached to said object near a corrosion area between said film and said object for determining a mass attenuation coefficient of said object and a conversion factor between density and thickness of said object;

means for scanning and digitizing said radiograph to generate digital information representing said object and said pair of shims;

means for displaying a graphical image of said object and said pair of shims based on said digital information; and means for processing said graphical image to obtain a numerical value representing the extent of corrosion in said object.

2. The apparatus according to claim 1, wherein said image processing means further provide a second numerical value representing the remaining wall thickness of said object.

3. The apparatus according to claim 1, wherein said film is wrapped around said object which is a pipe.

4. The apparatus according to claim 1, wherein said film is configured flat beyond said object which is a pipe.

5. The apparatus according to claim 4, wherein said film is in contact with said pipe.

6. The apparatus according to claim 4, wherein said film is spaced apart from said pipe.

7. The apparatus according to claim 1, wherein said radiation source is in contact with said object which is a pipe.

8. The apparatus according to claim 1, wherein said radiation source is spaced apart from said object which is a pipe.

9. The apparatus according to claim 1, wherein one shim of said pair of shims is thinner than the other shim of said pair.

10. The apparatus according to claim 1, wherein said shims are made of the same material as said object.

11. A non-destructive testing method for measuring corrosion or erosion in an object, comprising:

placing a radiation source adjacent said object for emitting rays directed at said object;

locating a radiation sensitive film substantially across and beyond said object from said radiation source for receiving said rays to produce a radiograph of said object;

attaching a pair of shims to said object near a corrosion area between said film and said object for determining a mass attenuation coefficient of said object and a conversion factor between density and thickness of said object;

scanning and digitizing said radiograph to generate digital information representing said object and said pair of shims;

displaying a graphical image of said object and said pair of shims based on said digital information; and processing said graphical image to obtain a numerical value representing the extent of corrosion in said object.

processing said graphical image to obtain a numerical value representing the extent of corrosion in said object.

12. The method according to claim 11, wherein said step of graphical image display further comprises the step of displaying at least one profile plot of said object, and is based on windows environment navigating a user through a multiple of windows requesting additional information regarding said object, said radiation source, said pair of shims and said film.

13. The method according to claim 11, wherein said step of graphical image processing comprises the step of calculating a mass attenuation coefficient of said object according to a formula $\Delta gs/gs = \mu_m p \Delta t_{gs}$, and the step of calculating a conversion factor between density and thickness of said object according to a second formula $t_{phys} = t_{gs} e^{mtgs}$.

* * * * *

UNITED STATES PATENT AND TRADEMARK OFFICE
CERTIFICATE OF CORRECTION

PATENT NO. : 5,864,601
DATED : January 26, 1999
INVENTOR(S): Cattorini et al.

It is certified that error appears in the above-identified patent and that said Letters Patent is hereby corrected as shown below:

Column 10,
    lines 12, 13, and 14 should be deleted, since they are duplicative of lines 9, 10, 11.

Signed and Sealed this

First Day of June, 1999

*Attest:*

Q. TODD DICKINSON

*Attesting Officer*      *Acting Commissioner of Patents and Trademarks*